Feb. 4, 1958 E. S. BOERNER Plant Pat. 1,679
CHRYSANTHEMUM PLANT
Filed May 27, 1957
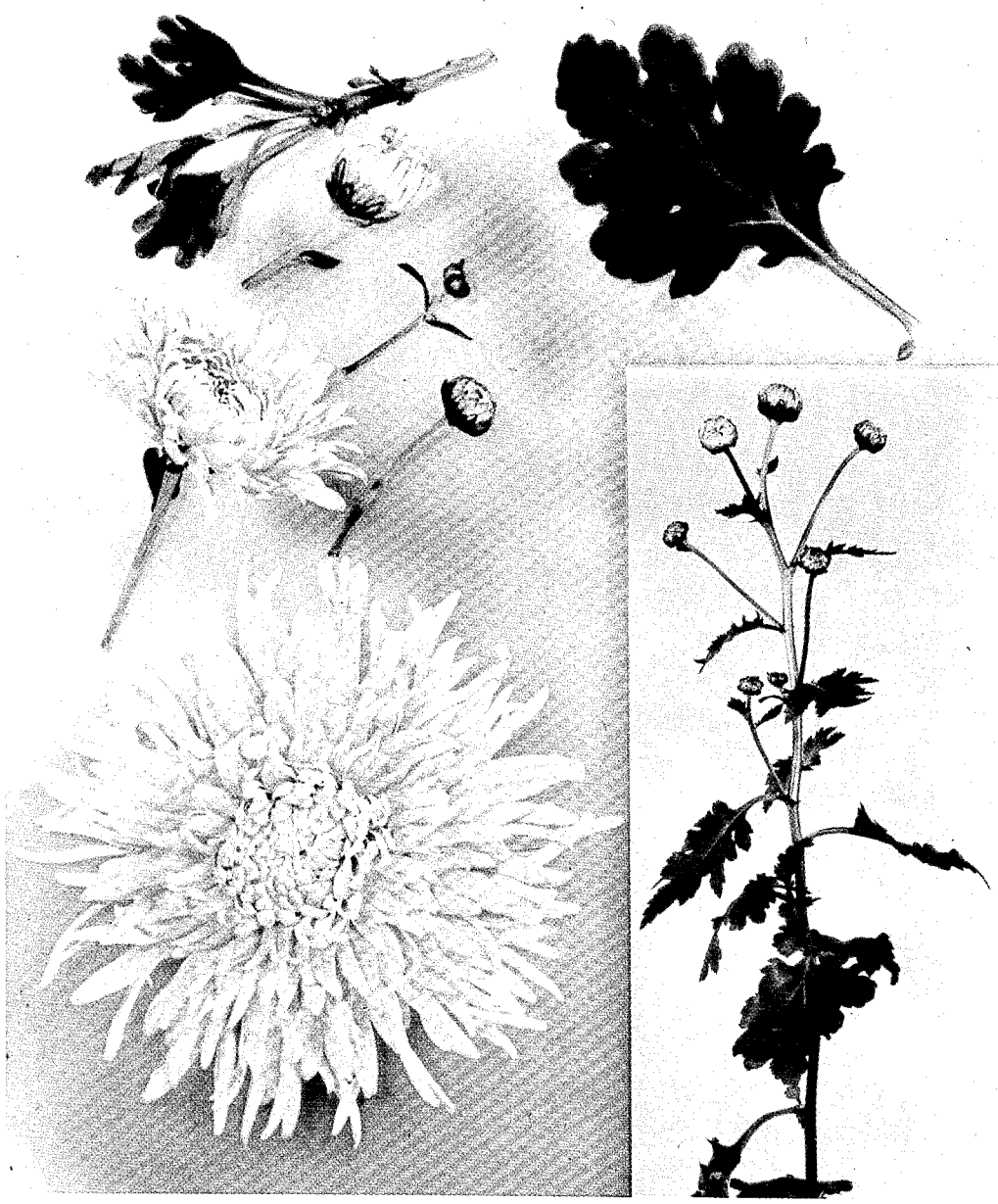
Inventor.
E. S. Boerner
By: Robb & Robb
Attorneys.

United States Patent Office

Plant Pat. 1,679
Patented Feb. 4, 1958

1,679

CHRYSANTHEMUM PLANT

Eugene S. Boerner, Newark, N. Y., assignor to Jackson & Perkins Company, Newark, N. Y., a corporation of New York Application May 27, 1957, Serial No. 661,984

1 Claim. (Cl. 47—60)

The present invention relates to a new and distinct variety of chrysanthemum plant of the decorative type, which was originated by me by crossing an unnamed and unpatented pink seedling derived from a cross of "Meadowlark" (Plant Patent No. 1,305) × "Thrush" (Plant Patent No. 1,168) with the variety "Grosbeak" (Plant Patent No. 1,132).

The primary objective of this breeding was to produce a new chrysanthemum variety which combines the flower size and firmness of the unnamed seedling parent with the flower color of the parent variety "Grosbeak." This objective was fully achieved, along with other improved features, as evidenced by the following characteristics which are outstanding in the new variety and which represent a unique combination in a chrysanthemum of this class:

(1) Attractive plant and flowers;

(2) Good flower size and firmness, corresponding to that of the unnamed seedling parent;

(3) Long and narrow petal form; and (4) The distinctive Pale Rhodonite Pink general color tonality of the flowers, with individual petal margins edged with Rhodonite Pink.

The foregoing characteristics and distinctions definitely differentiate the new variety from its parents, as well as from all other varieties of its class of which I am aware, and asexual reproduction of the new variety by both top cuttings and underground runners, as performed at Newark, New York, shows that these characteristics and distinctions come true to form and are established and transmitted through succeeding propagations.

The accompanying drawing shows typical specimens of the vegetative growth and flowers of my new variety in different stages of development, and as depicted in color as nearly true as it is reasonably possible to make the same in a color illustration of this character, as well as a typical specimen plant which is depicted in black-and-white, as illustrative of the form and habit of growth of the plant.

The following is a detailed description of my new variety, with color terminology in accordance with Ridgway's Color Standards and Nomenclature, as based upon observations made from specimens grown outdoors at Newark, New York, near mid-afternoon in the latter part of the month of September:

Parentage: An unnamed pink seedling derived from a cross of "Meadowlark" × "Thrush" × "Grosbeak."

Classification: Decorative.

Growth: Upright; attains a height averaging about 24 inches.

Cold resistance: The plant is very winter hardy in northern New York; flowers are frost-resistant.

Blooming period: In the Newark, New York, climatic area, blooming begins about September 27th and continues until frosts.

*Flower*

Bud:

*Color.*—When sepals first divide—Pale Rhodonite Pink, Plate 38. When petals begin to unfurl—Cameo Pink, Plate 26. When half-blown: Inside of petals—Rosolane Pink, Plate 26, lightly overcast with Rhodonite Pink, Plate 38, on the outer edge of the petals; reverse of petals—Cameo Pink, Plate 26, lightly overcast with Pale Rosolane Purple, Plate 26.

*Peduncle.*—Strong. Color—Kildare Green, Plate 31.

Bloom:

*Size.*—From 4½ to 5 inches.

*Stem.*—Strong.

*Form.*—Decorative.

*Petalage.*—Double.

*Color.*—Center of flower—Rhodonite Pink, Plate 38, lightly overcast with Pale Rhodonite Pink, Plate 38. Outer petals—Pale Rhodonite Pink, Plate 38. Base of petals—Bright Chalcedony Yellow, Plate 17. Inside of petals—Pale Rhodonite Pink, Plate 38, with edges of petal Rhodonite Pink, Plate 38. Reverse of petals—Cameo Pink, Plate 26.

*Petals.*—Texture—stiff. Form—long; narrow.

*Fragrance.*—Characteristic chrysanthemum.

*Plant*

Form: Compact; bushy.

Growth: Free.

Foliage:

*Size.*—Medium.

*Quantity.*—Normal.

*Color.*—Upper side—Deep Dull Yellow-Green, Plate 31. Reverse side—Rainette Green, Plate 31.

*Texture.*—Leathery; glossy.

I claim:

A new and distinct variety of chrysanthemum plant of the decorative type, substantially as herein shown and described, characterized particularly as to novelty by the attractiveness of its plant and flowers, the large size and firmness of its flowers, the long and narrow form of its flower petals, and the distinctive Pale Rhodonite Pink general color tonality of its flowers, with the margins of the individual petals edged with Rhodonite Pink.

No references cited.